United States Patent
Ishiguro et al.

(10) Patent No.: US 9,064,768 B2
(45) Date of Patent: Jun. 23, 2015

(54) IMAGING APPARATUS AND MEDICAL EQUIPMENT

(71) Applicant: SEIKO EPSON CORPORATION, Tokyo (JP)

(72) Inventors: Hideto Ishiguro, Nagano (JP); Tsukasa Eguchi, Nagano (JP); Tetsuji Fujita, Nagano (JP); Hidetoshi Yamamoto, Nagano (JP)

(73) Assignee: Seiko Epson Corporation, Tokyo (JP)

( * ) Notice: Subject to any disclaimer, the term of this patent is extended or adjusted under 35 U.S.C. 154(b) by 79 days.

(21) Appl. No.: 14/041,400

(22) Filed: Sep. 30, 2013

(65) Prior Publication Data

US 2014/0091328 A1 Apr. 3, 2014

(30) Foreign Application Priority Data

Oct. 1, 2012 (JP) .................................. 2012-219278

(51) Int. Cl.
*H01L 27/15* (2006.01)
*H01L 29/161* (2006.01)
(Continued)

(52) U.S. Cl.
CPC ........ *H01L 27/14629* (2013.01); *G06K 9/0004* (2013.01); *A61B 5/1455* (2013.01)

(58) Field of Classification Search
USPC .............................. 257/13, 40, 79–103, 918,
257/E51.015–E51.022, E31.058, E31.03,
257/E31.115, E25.032, E27.133–E27.139,
257/252–254, 257–258, 22, 184, 431, 432,
257/642, 643, 759, E37.007,
257/E51.001–E51.052, E27.117–E27.119;
438/22–47, 69, 493, 503, 507, 956, 82,
438/99, 16, 65; 348/77, 342, E07.085,
348/E05.024; 382/115, 124, 125, 126
See application file for complete search history.

(56) References Cited

U.S. PATENT DOCUMENTS 6,941,002 B1 9/2005 Kawahara et al.
6,970,234 B2 11/2005 Nagasaka et al.
(Continued)

FOREIGN PATENT DOCUMENTS

JP 2001-052151 A 2/2001
JP 2003-030632 A 1/2003
(Continued)

*Primary Examiner* — Dao H Nguyen
*Assistant Examiner* — Tram H Nguyen
(74) *Attorney, Agent, or Firm* — Global IP Counselors, LLP (57) ABSTRACT

A light receiving section is provided with a plurality of light receiving elements. A light source section is arranged in a subject side of the light receiving section, and is provided with a light emitting section that illuminates the subject and a plurality of transmissive sections that transmits incident light to the light receiving section side. The light emitting section is provided with a first translucent layer, which includes a light emitting layer, and a reflection layer and a semi-transmissive reflection layer, which are opposed each other interposing the first translucent layer, so that a resonance structure that resonates irradiation light from the light emitting layer is formed. Each of the transmissive sections is provided with a second translucent layer, and a first semi-transmissive reflection layer and a second semi-transmissive reflection layer, which are opposed each other interposing the second translucent layer, so that a resonance structure that resonates incident light from the subject side is formed. A resonance length between the reflection layer and the semi-transmissive reflection layer in the light emitting section is more than a resonance length between the first semi-transmissive reflection layer and the second semi-transmissive reflection layer in the transmissive section.

10 Claims, 5 Drawing Sheets

(51) Int. Cl.
*H01L 31/12* (2006.01)
*H01L 31/153* (2006.01)
*H01L 33/00* (2010.01)
*H01L 27/146* (2006.01)
*G06K 9/00* (2006.01)
*A61B 5/1455* (2006.01)

(56) References Cited

U.S. PATENT DOCUMENTS

| | | | |
|---|---|---|---|
| 7,728,902 B2 | 6/2010 | Kishigami et al. | |
| 7,936,983 B2 | 5/2011 | Konno et al. | |
| 8,085,312 B2 * | 12/2011 | Morita et al. | 348/222.1 |
| 8,102,118 B2 * | 1/2012 | Lee et al. | 313/506 |
| 8,665,357 B2 * | 3/2014 | Ishiguro et al. | 348/340 |
| 2007/0075305 A1 * | 4/2007 | Miyata et al. | 257/13 |
| 2012/0242884 A1 | 9/2012 | Ishiguro et al. | |
| 2012/0256089 A1 | 10/2012 | Kanda et al. | |
| 2012/0257031 A1 * | 10/2012 | Tsuchiya et al. | 348/77 |

FOREIGN PATENT DOCUMENTS

| | | |
|---|---|---|
| JP | 2008-036058 A | 2/2008 |
| JP | 2009-003821 A | 1/2009 |
| JP | 2009-110452 A | 5/2009 |
| JP | 2009-172263 A | 8/2009 |
| JP | 2012-199868 A | 10/2012 |
| JP | 2012-221082 A | 11/2012 |
| JP | 2012-221083 A | 11/2012 |
| JP | 2012-221141 A | 11/2012 |
| JP | 2012-222483 A | 11/2012 |
| JP | 2012-222484 A | 11/2012 |
| JP | 2013-084173 A | 5/2013 |

* cited by examiner

Fig. 15 ined with respect to the surface of the subject 90, the shadows that the surface structure of the subject 90 (e.g., fingerprints or wrinkles) was reflected is emphasized. Thus, it is difficult to take a fine and clear image of veins that are the inside of the subject 90. Considering the situation described above, the advantage of the invention is to take an image of a subject by suppressing glares or shadows.

Means Used to Solve the Above-Mentioned Problems

In order to solve the problem described above, an imaging apparatus of the invention is provided with a light receiving section in which a plurality of light receiving elements is arranged, and a light source section arranged in a subject side of the light receiving section and including a light emitting section that emits light toward the subject and a plurality of transmissive sections where the incident light from the subject side is transmitted to each light receiving element side. The light emitting section includes a first translucent layer having light permeability, which includes a light emitting layer, a semi-transmissive reflection layer located in the subject side of the first translucent layer, and a reflection layer, which is opposed to the semi-transmissive reflection layer interposing the first translucent layer. A resonation structure is formed so that the light emitted from the light emitting layer is resonated between the semi-transmissive reflection layer and the reflection layer. The plurality of the transmissive sections respectively includes a second translucent layer having light permeability, and a first semi-transmissive reflection layer and a second semi-transmissive reflection layer that are opposed each other interposing the second translucent layer. A resonation structure is formed so that the irradiation light from the light emitting layer is resonated between the first semi-transmissive reflection layer and the second semi-transmissive reflection layer. A first resonant length (e.g., resonant length L1) between the reflection layer and the semi-transmissive reflection layer in the light emitting section is more than a second resonance length (e.g., resonant length L2) between the first semi-transmissive reflection layer and the second semi-transmissive reflection layer in the transmissive section. In the above structure, the first resonant length of the resonant structure of the light emitting section is more than the second resonant length of the resonant structure of the transmissive section so as to approach between a peak wavelength (e.g., peak wavelength $\lambda 1$) of the irradiation intensity from the light emitting section in a direction inclined with respect to a reference direction, which is perpendicular to the reflection surface of the resonant structure, and a peak wavelength (e.g., peak wavelength $\lambda 2$) of the irradiation intensity from the transmissive section with respect to the reference direction in comparison with the case that the first resonant length and the second resonant length are matched each other. That is, an imaging light in a specific wavelength is emitted from the light emitting section in a direction inclined with respect to the reference direction and passes through the transmissive section in a direction parallel to the reference direction so that it progresses to the light receiving section side. Therefore, it is possible to take a fine and clear image of the subject by suppressing glares or shadows on the surface of the subject.

In a preferred aspect of the invention, the first resonant length and the second resonant length are set so as to match between the peak wavelength (e.g., peak wavelength $\lambda 1$) of the irradiation intensity from the light emitting section in the direction inclined with respect to the reference direction and the peak wavelength (e.g., peak wavelength $\lambda 2$) of the irradiation intensity from the transmissive section with respect to the reference direction. In the above aspect, it becomes particularly remarkable for the effect that a fine and clear image of a subject can be taken while suppressing glares and shadows of the surface of the subject. By the way, the phrase "the peak wavelength of the irradiation intensity from the light emitting section and the peak wavelength of the irradiation intensity from the transmissive section are matched" means that in addition to the case that each peak wavelength is totally matched, it includes the case that each peak wavelength is substantively matched (for example, in a case that their difference is within a range of manufacturing error).

The imaging apparatus according to the preferred aspect of the invention is provided with a plurality of lenses which is arranged in the subject side of the light source section so that the incident light from the subject side is focused to each of the light receiving elements. In the above aspect, the plurality of lenses s arranged so that the incident light from the subject side is focused to each of the light receiving elements. Thus, it is possible to improve the use efficiency of the imaging light in comparison with a configuration that the incident light from the subject is not focused.

In a preferred aspect of the invention, an angle in an irradiation direction with respect to a reference direction (e.g., target angle θx) is more than or equal to 30° and less than or equal to 60° (for example, 45°). According to the configuration described above, it is possible to suppress glares or shadows while the use efficiency of the incident light from the light emitting section maintains in a high level.

In a preferred aspect of the invention, the reflection layer of the light emitting section includes a basic reflection layer having light reflectivity, and a dielectric multilayer film. The first semi-transmissive reflection layer of the transmissive section includes the dielectric multilayer film and it does not include the basic reflection layer. According to the configuration described above, the dielectric multilayer film of the reflection layer of the light emitting section and the dielectric multilayer film of the first semi-transmissive reflection layer of the transmissive section are formed in the same layer so that it has an advantage that the manufacturing process is simplified in comparison with the case that the reflection layer of the light emitting section and the first semi-transmissive reflection layer of the transmissive section are formed independently of each other. Also, by the configuration that the dielectric multilayer film includes a layer formed by amorphous silicon, visible light is blocked by the layer of the amorphous silicon so that it has an advantage that it is not necessary to independently provide an optical filter that blocks the visible light.

In a preferred aspect of the invention, the semi-transmissive reflection layer of the light emitting section and the second semi-transmissive reflection layer of the transmissive section are formed in the same process and are formed by a material having light reflectivity. In the above configuration, the semi-transmissive reflection layer and the second semi-transmissive reflection layer of the transmissive section are formed in the same process so that it has an advantage that the manufacturing process is simplified in comparison with the case that the semi-transmissive reflection layer and the second transmissive reflection layer are formed independently of each other. A reflection conductive layer used as the semi-transmissive reflection layer and the second transmissive reflection layer is formed by the mixture of, for example, magnesium and silver. It is particularly preferable that the ratio of silver is more than the ratio of magnesium.

In a preferred aspect of the invention, the first translucent layer of the light emitting section includes a transparent electrode layer, which has light permeability, and light emitting layer. The second translucent layer of the transmissive section includes the light emitting layer and does not include the transparent electrode layer. According to the configuration described above, the light emitting layer of the first translucent layer of the light emitting section and the light emitting layer of the second translucent layer are formed in the same layer so that it has an advantage that the manufacturing process is simplified in comparison with the case that the first translucent layer of the light emitting section and the second translucent layer are formed independently of each other.

The imaging apparatus according to each of the aspects described above is preferably used in various types of electronic equipment. Specific examples of the electronic equipment include a biometric authentication apparatus which executes biometric authentication using an image of veins which has been imaged by the imaging apparatus, and a medical equipment (a biometric information estimating apparatus such as a blood alcohol concentration estimating apparatus, a blood sugar level estimating apparatus, and the like) which estimates biometric information for blood alcohol concentration, blood sugar level, and the like from images which have been imaged by the imaging apparatus.

BRIEF DESCRIPTION OF THE DRAWINGS

Referring now to the attached drawings which form a part of this original disclosure.

DETAILED DESCRIPTION OF EXEMPLARY EMBODIMENTS

Embodiment

Figure 1:
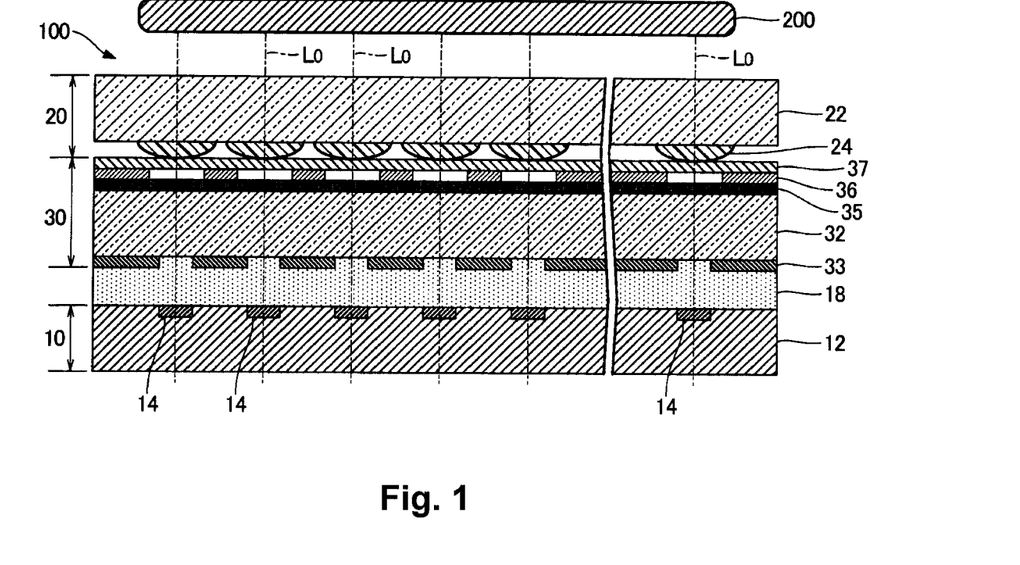
FIG. 1 is a cross-sectional diagram of an imaging apparatus according to an embodiment of the invention.
Figure 2:
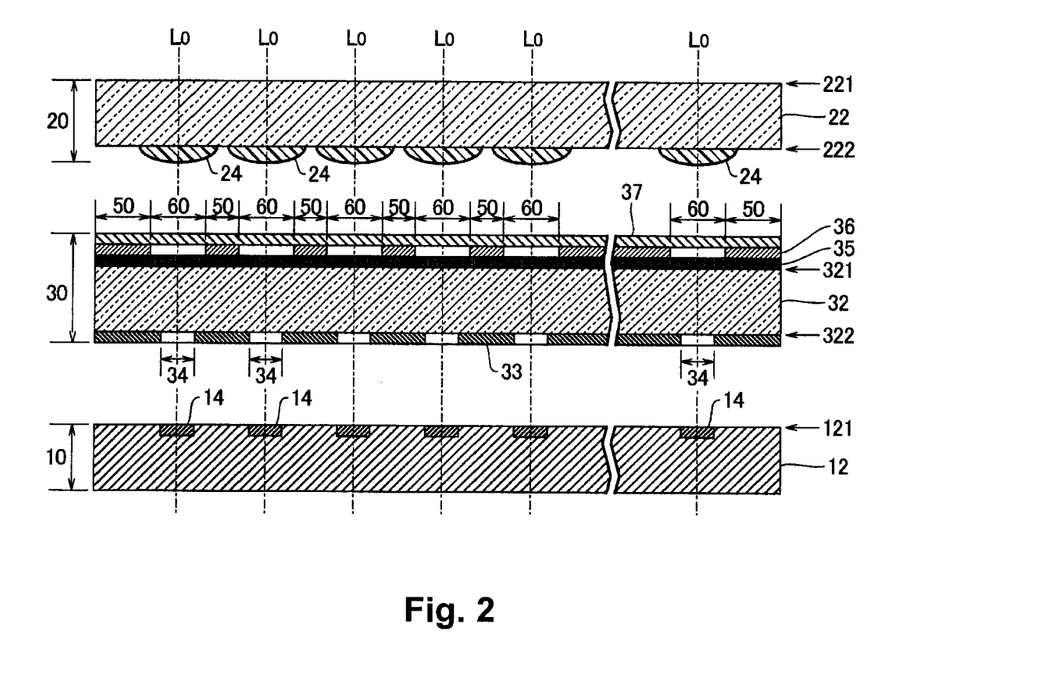
FIG. 2 is an exploded cross-sectional diagram of the imaging apparatus.

FIG. 1 is a cross-sectional diagram of an imaging apparatus 100 according to one embodiment of the invention. FIG. 2 is an exploded cross-sectional diagram of the imaging apparatus 100. The imaging apparatus 100 of the present embodiment is a sensing apparatus which images a subject 200 in a state in which illumination light with a specific wavelength (referred to below as "imaging light") is irradiated, and for example, is preferably used as a biometric authentication apparatus (vein sensor) which images an image of veins in a living body (typically, a human finger). The imaging light is a predetermined frequency of an optic element where the intensity becomes a peak near a specific wavelength $\lambda$ (hereinafter referred to as "imaging wavelength"). It gives an example that the imaging wavelength $\lambda$ is 850 nm of near-infrared light below, but the imaging wavelength can be appropriately changed in response to the optical properties (transmittance or reflectance), and the like.

As shown in FIG. 1 and FIG. 2, the imaging apparatus 100 of the invention is provided with a light receiving section 10, light focusing section 20, and a light emitting section 30. The light emitting section 30 is arranged in a subject 200 side of the light receiving section 10 (between the light receiving section 10 and the subject 200), and the light focusing section 20 is arranged in the subject 200 side of the light emitting section 30 (between the light emitting section 30 and the subject 200). That is, the light emitting section 30 is located between the light receiving section 10 and the light focusing section 20. Schematically, the incident light from the subject 200 that was illuminated by imaging light emitted from the light emitting section 30 is focused in the light focusing section 20 and passes through the light emitting section 30 and reaches to the light receiving section 10.

Figure 3:
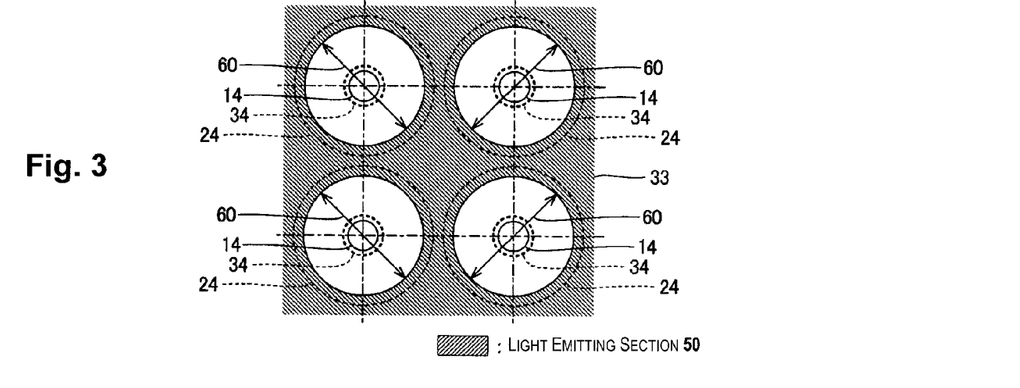
FIG. 3 is a planar diagram illustrating a relationship between each element of the imaging apparatus.

The light receiving section 10 is an element that images the subject 200 and is configured to include a substrate 12 and a plurality of light receiving elements 14. The substrate 12 is a member with a plate shape which is formed from, for example, a semiconductor material. The plurality of light receiving elements 14 are formed on a surface (acceptance surface) 121 on the subject 200 side of the substrate 12, and are ordered in a matrix formation in a planar view (that is, when viewed from a direction which is perpendicular to the surface 121) as shown in FIG. 3. Each of the plurality of light receiving elements 14 generates a detection signal according to the amount of imaging light. An image of the subject 200 is generated by an image processing of the detection signal that was generated in each of the plurality of light receiving elements 14. For example, a Complementary Metal Oxide Semiconductor (CMOS) sensor or a Charge Coupled Device (CCD) sensor which is well known is preferably used as the light receiving section 10.

The light focusing section 20 in FIG. 1 is an element which focuses imaging light that arrives from the subject 200, and is configured to include a substrate 22 and a plurality of lenses (microlenses) 24. As shown in FIG. 2, the substrate 22 is an optically transmissive (a property whereby it is possible for imaging light to pass through) member with a plate shape which includes a surface 221 which opposes the subject 200 and a surface 222 on the opposite side to the surface 221. For example, a glass substrate or a quartz substrate is preferably adopted as the substrate 22. The plurality of lenses 24 are formed on the surface 222 of the substrate 22. Each of the lenses 24 is a convex lens which focuses imaging light which is incident from the subject 200 onto the surface 221 of the substrate 22 and passes through the substrate 22.

Figure 4:
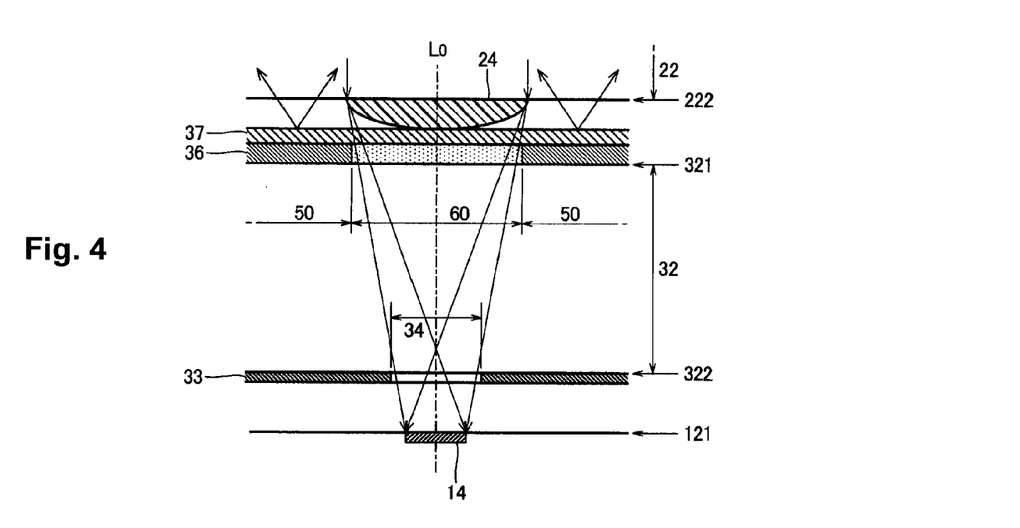
FIG. 4 is a cross-sectional diagram where the imaging apparatus is partially enlarged.

FIG. 4 is a cross-sectional diagram of a part corresponding to one light receiving element 14 in the imaging elements. As shown in FIG. 1 and FIG. 4, each lens 24 of the light focusing section 20 and each light receiving element 14 of the light receiving section 10 are one to one correspondence. Specifically, as shown in FIG. 4, a light axis L0 of each lens 24 passes through the light receiving element 14 (typically, a center of a light sensing area of the light receiving element 14) corresponding to the lens 24. Therefore, the plurality of lenses 24 is arranged in matrix formation in a planer view in a similar manner as each light receiving element 14 as shown in FIG. 3. For example, an arbitrary manufacturing technique of such as a method (reflow method) where each of the lenses 24 is formed by heat deforming numerous fine resists which are formed on the substrate 22, a method where each of the lenses 24 is formed by a photolithography process which uses an area gradation mask, a method where the substrate 22 and each of the lenses 24 are integrally formed by polishing and molding a member with a plate shape, or the like is adopted in the manufacturing of each of the lenses 24.

The light emitting section 30 in FIG. 1 has an element that imaging light is generated and the subject 200 is illuminated and the imaging light, which was focused in each lens 24, passes to each light receiving element 14 side, and is configured to include a substrate 32, a light blocking layer 33, a wiring layer 35, a light source section 36, and a protection layer 37. As shown in FIG. 2, the substrate 32 is an optically transmissive member with a plate shape (for example, a glass substrate or a quartz substrate) which includes a surface 321 which opposes the light focusing section 20 (each of the lenses 24) and a surface 322 on the opposite side to the surface 321. The light blocking layer 33 is a film body having a light blocking effect (a property to absorb or reflect imaging light) and is formed on the surface 322 of the substrate 32. For example, the light blocking layer 33 is formed by a resin material in which a black agent (black pigment) such as, for example, carbon black, and the like is dispersed, or a metal material such as chrome, and the like having the light blocking effect. As shown in FIG. 2 and FIG. 4, a plurality of circular-shaped opening sections 34 is formed on the light blocking layer 33. Each of the opening sections 34 of the light blocking layer 33 and each of lenses 24 of the light focusing section 20 (or each of the light receiving elements 14 of the light receiving section 10) are one to one correspondence. Specifically, as shown in FIG. 4, the light axis L0 in each of the lenses 24 passes through the opening section 34, which corresponds to the lens 24 (typically, it passes through a center of the opening section 34). Therefore, as shown in FIG. 3, each of the opening sections 34 is arranged in a matrix formation in a planar view in a similar manner as each of the lenses 24 or each of the light receiving elements 14.

The wiring layer 35 is formed on the surface 321 of the substrate 32, and is configured to include a wire for supplying electric current to the light source section 36. The light source section 36 is formed on the surface of the wiring layer 35, and illuminates the subject 200. The imaging light from the subject 200 side passes to each light receiving element 14 side. As shown in FIG. 2 and FIG. 4, the light source section 36 is separated into a light emitting section 50 and a plurality of transmissive sections 60 in a planer view (that is, it is in a state of viewing in a direction perpendicular to the surface 321 of the substrate 32). The light emitting section 50 generates and emits imaging light to illuminate the subject 200. The plurality of transmissive sections 60 respectively transmits the incident light from the subject 200 side to each of the light receiving elements 14 side. As shown in FIG. 3, each of the transmissive sections 60 is formed in a circular shape in a planer view. Each of the transmissive sections 60 of the light source section 36 and each of the lenses 24 of the light focusing section 20 (or each of the light receiving elements 14 of the light receiving section 10) are one to one correspondence. Specifically, as shown in FIG. 4, the light axis L0 of each of the lenses 24 passes through the transmissive sections 60 (typically, it passes through a center of the transmissive section 60) corresponding to the lens 24. Therefore, as shown in FIG. 3, each of the transmissive sections 60 is arranged in a matrix formation in a planer view in a similar manner as each of the lenses 24 or the light receiving elements 14. Each of wirings in the wiring layer 35 is formed in a region overlapping with the light emitting section 50 in a planer view, and it does not overlap with each of the transmissive sections 60. The protection layer 37 in FIG. 1 has an element (sealing layer) to protect from external air or fluid by sealing the light source section 36, and it is formed by an insulating material having light permeability (e.g., resin material).

The light receiving section 10 and the light emitting section 30 are mutually fixed with a space by, for example, an adhesive agent 18 having light permeability. Also, the respective peripheries of the light focusing section 20 and the light emitting section 30 are mutually fixed. In FIG. 1 and FIG. 4, a configuration that the light focusing section 20 and the light emitting section 30 are connected to contact the surface of each of the lenses 24 of the light focusing section 20 and the surface of the protection section 30 of the light emitting section 30 is exemplified. However, it is possible to mutually fix the light focusing section 20 and the light emitting section 30 so as to oppose each other with a space mutually between the surface of each of the lenses 24 and the surface of the protection layer 37. Also, it is possible to mutually fix the light focusing section 20 and the light emitting section 30 by using an adhesive agent having light permeability that has a small refraction index in comparison with the material of each of the lenses 24.

In the configuration described above, the imaging light which is output from the light emitting section 50 in the light source section 36 passes through the light focusing section 20 (the substrate 22 and each of the lenses 24) and irradiates the subject 200, passes through or is reflected by veins inside the subject 200 and is incident on the light focusing section 20, and passes through the transmissive sections 60 of the light source section 36 and the opening sections 34 in the substrate 32 and the light blocking layer 33 after having been focused by each of the lenses 24 and reaches the light receiving element 14. Accordingly, an image of veins in the subject 200 is imaged.

In the configuration as described above, since the light source section 36 is arranged between each of the light receiving elements 14 in the light receiving section 10 and the subject 200, it is easy to reduce the size of the apparatus in comparison to the technique in Patent Document 1 where a light source section and an imaging section are arranged so as to oppose each other interposing the subject. In addition, since the light emitting section 50 which irradiates imaging light onto the subject 200 is distributed in a planar form, it is possible to reduce uneven distribution of the amount of irradiating light with regard to the subject 200 (to uniformly illuminate the subject 200) in comparison to a case where a point light source such as a Light Emitting Diode (LED), and the like being used to illuminate the subject 200. Moreover, in the present embodiment, since the imaging light from the subject 200 which is illuminated by the light source section 36 reaches the light receiving element 14 after having been focused by each of the lenses 24 in the light focusing section 20, there is an advantage in that it is possible to secure a sufficient amount of light which reaches from the subject 200 to each of the light receiving elements 14 in comparison to the technique in Patent Document 2 where there is no element which focuses the imaging light.

Figure 5:
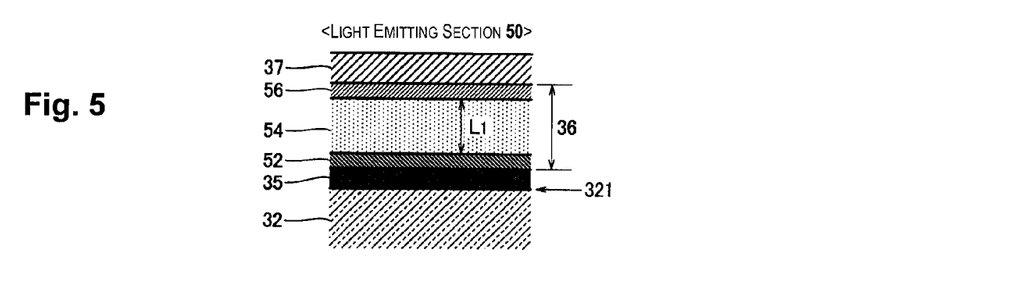
FIG. 5 is a cross-sectional diagram of a light emitting section in a light source section of the imaging apparatus.

FIG. 5 is a cross-sectional diagram that a light emitting section 50 in a light source section 36 is enlarged. As shown in FIG. 5, the light emitting section 50 is configured to include a reflection layer 52, a first translucent layer 54, and a semi-transmissive reflection layer 56. The reflection layer 52 is formed on the surface (on the light receiving section 10 side viewed from the first translucent layer 54) of the wiring layer 35, and the first translucent layer 54 is formed on the surface of the reflection layer 52, and the semi-transmissive reflection layer 56 is formed on the surface (on the subject 200 side viewed from the first translucent layer 54) of the first translucent layer 54. That is, the reflection layer 52 and the semi-transmissive reflection layer 56 are opposed each other interposing the first translucent layer 54.

The first translucent layer 54 is a thin film having light permeability that includes the light emitting layer which generates imaging light. The reflection layer 52 is a thin film having light reflectivity so as to reflect the imaging light, which is emitted from the light emitting layer and progresses to the light receiving section 10, to the subject 200 side. The semi-transmissive reflection layer 56 is a thin film (half mirror) having semi-transmissive reflectivity so as to transmit a part of the imaging light, which arrives from the first translucent layer 54, (imaging light that the light emitting layer generates and progresses to the subject 200 side, or imaging light reflected in the reflection layer 52) and to reflect the remaining.

As described above, the reflection layer 52 and the semi-transmissive reflection layer 56 are opposed each other interposing the first translucent layer 54 so that the resonation structure (microcavity) that resonates the imaging light, which is emitted from the light emitting layer of the first translucent layer 54, between the reflection layer 52 and the semi-transmissive reflection layer 56. That is, the light emitted from the light emitting layer is reciprocated between the reflection layer 52 and the semi-transmissive reflection layer 56, and passes through the semi-transmissive reflection layer 56 and is emitted to the subject 200 after a resonance component of a wavelength in response to an optical distance L1 (hereinafter referred to as "resonance length") between the reflection layer 52 and the semi-transmissive reflection layer 56 was alternatively amplified. That is, the light emitting section 50 functions as a bandpass filter that alternatively emphasizes a wavelength component in response to the resonance length L1 in the imaging light that the light emitting layer generates. The resonance length L1 corresponds to a film thickness of the first translucent layer 54.

Figure 6:
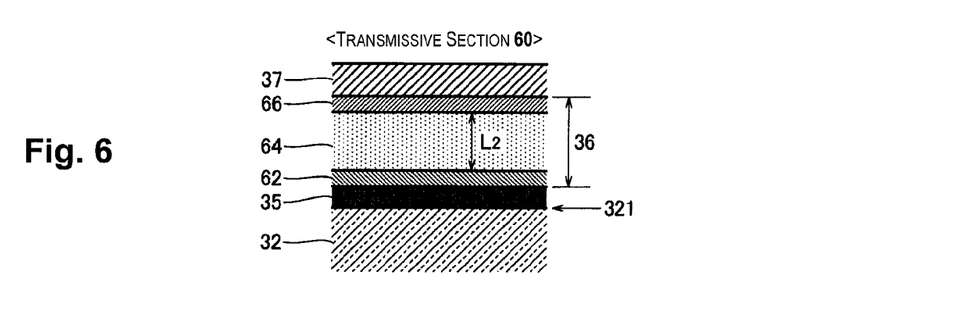
FIG. 6 is a cross-sectional diagram of a transmissive section in the light source section of the imaging apparatus.

FIG. 6 is a cross-sectional diagram that the transmissive section 60 in the light source section 36 is enlarged. As shown in FIG. 6, the transmissive section 60 is configured to include a first semi-transmissive reflection layer 62, a second translucent layer 64, and a second semi-transmissive reflection layer 66. The first semi-transmissive reflection layer 62 is formed on the surface (on the light receiving section 10 side viewed from the second translucent layer 64) of the wiring layer 35, and the second translucent layer 64 is formed on the surface of the first semi-transmissive reflection layer 62, and the second semi-transmissive reflection layer is formed on the surface (on the subject 200 side viewed from the second translucent layer 64) of the second translucent layer 64. That is, the first semi-transmissive reflection layer 62 and the second semi-transmissive reflection layer 66 are opposed each other interposing the second translucent layer 64.

The second translucent layer 64 is a thin film having light permeability. The first semi-transmissive reflection layer 62 is a thin film (half mirror) having semi-transmissive reflectivity so as to pass through a part of the imaging light, which progresses the inside of the second translucent layer 64 to the light receiving section 10 side, to the light receiving section side 10 and reflect the remaining to the subject 200 side (the second semi-transmissive reflection layer 66 side). The second semi-transmissive reflection layer 66 is a thin film (half mirror) having semi-transmissive reflectivity so as to transmit a part of the imaging light, which was focused in each of the lenses 24 of the light focusing section 20 and from the subject 200 side, and take it inside of the second translucent layer 64, and reflect a part of the imaging light, which is reflected in the first semi-transmissive reflection layer 62 and progresses to the subject 200 side, to the subject 200 side.

As described above, the first semi-transmissive reflection layer 62 and the second semi-transmissive reflection layer 66 are opposed each other interposing the second translucent layer 64 so as to form a resonant structure that resonates imaging light, which was focused in each of lenses 24 of the light focusing section 20 and from the subject 200, between the first semi-transmissive reflection layer 62 and the second semi-transmissive reflection layer 66. That is, the imaging light, which arrives from the subject 200 side and transmits through the second semi-transmissive reflection layer 66, is reciprocated between the first semi-transmissive reflection layer 62 and the second semi-transmissive reflection layer 66, and a resonance component of a wavelength in response to a resonance length (optical distance) L2 between the first semi-transmissive reflection layer 62 and the second semi-transmissive reflection layer 66 is alternatively amplified and passes through the first semi-transmissive reflection layer 62 and emits to the light receiving section 10 side. That is, the transmissive section 60 functions as a bandpass filter that alternatively emphasizes a wavelength component in response to the resonance length L2. The resonance length L2 corresponds to the film thickness of the second translucent layer 64.

Figure 7:
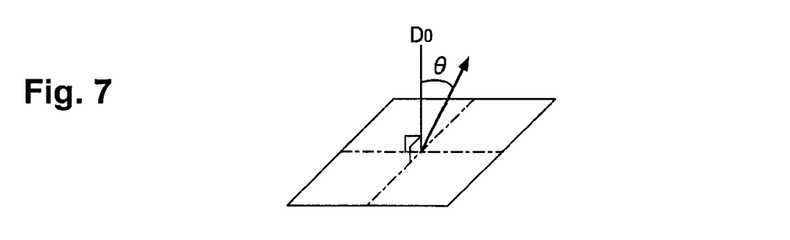
FIG. 7 is an explanatory diagram of an irradiation angle of imaging light.

By the way, a relationship between the wavelength and the strength of the irradiation light from the resonance structure (a wavelength that the strength is amplified in the resonance structure) depends on an irradiation angle $\theta$ of irradiation light. As shown in FIG. 7, the irradiation angle $\theta$ means an angle with respect to a reference direction D0 perpendicular to the reflection surface of the resonance structure. The reference direction D0 is a direction (a direction parallel to a light axis L0 of each of lenses 24 of the light focusing section 20) perpendicular to the surface 121 of the substrate 12.

Figure 8:
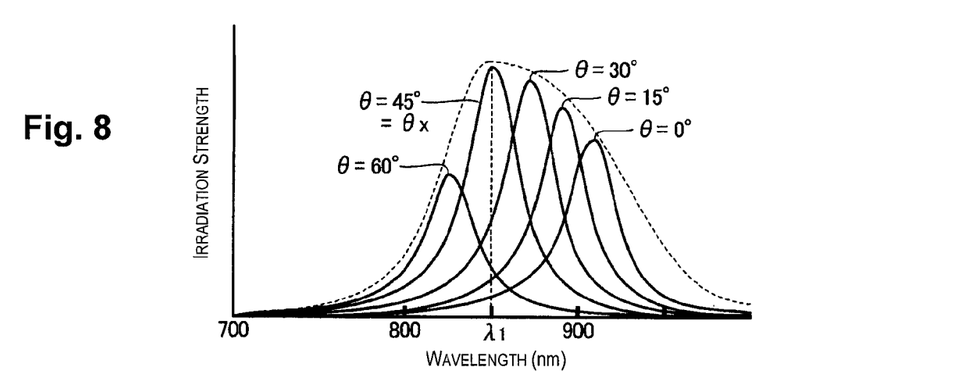
FIG. 8 is a graph showing a relationship between irradiation intensity and a wavelength from the light emitting section in every irradiation angle.

FIG. 8 is a graph showing a relationship between a wavelength and strength of the irradiation light from the resonance structure of the light emitting section 50 in the light source section 36 in a plurality of irradiation angles $\theta$ (74=0, 15, 30, 45, 60 [°]). In FIG. 8, the spectral characteristics of internal luminescence of the light emitting layer are described in a broken line. As is understood from FIG. 8, as the irradiation angle $\theta$ of the irradiation light from the resonance structure increases, the wavelengths in which the irradiation strength becomes a peak (hereinafter referred to as "peak wavelength") tends to be reduced. Also, as the resonance length L1 of the resonance structure of the light emitting section 50 reduces, a peak wavelength of the emitted light tends to be shifted to a short wavelength side.

Figure 14:
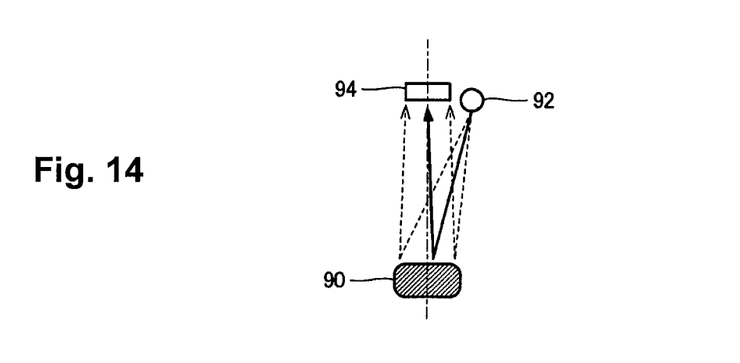
FIG. 14 is an explanatory diagram of a shadow that becomes apparent when a subject is illuminated in a small incident angle.

As described above in reference to FIG. 14, when the light is illuminated to the surface of the subject 200 in a small incident angle (an angle close to the front direction), the glare that a specific region of the surface of the subject 200 becomes extremely high brightness becomes significant. Therefore, in view of preventing it from the glare, it is preferred that a peak wavelength 2.1 of the irradiation strength for the illumination direction that inclines in a specific angle $\theta x$ (hereinafter referred to as "target angle") with respect to the reference direction D0 ($\theta=0°$) matches with an imaging wavelength $\lambda$.

In consideration of the above tendency, in the present embodiment, as shown in FIG. 8, the resonance length L1 of the resonance structure of the light emitting section 50 is selected so that a peak wavelength $\lambda 1$ of the irradiation strength from the light emitting section 50 in the illumination direction of the target angle $\theta x$ matches with (or comes close to) a desired imaging wavelength $\lambda$ (850 nm). That is, the imaging light of the imaging wavelength $\lambda$ in the light emitted from the light emitting layer is emitted in the illumination direction that inclines in the target angle $\theta x$ with respect to the reference direction D0. In FIG. 8, a case that the target angle $\theta x$ was set to 45° is exemplified.

Figure 9:
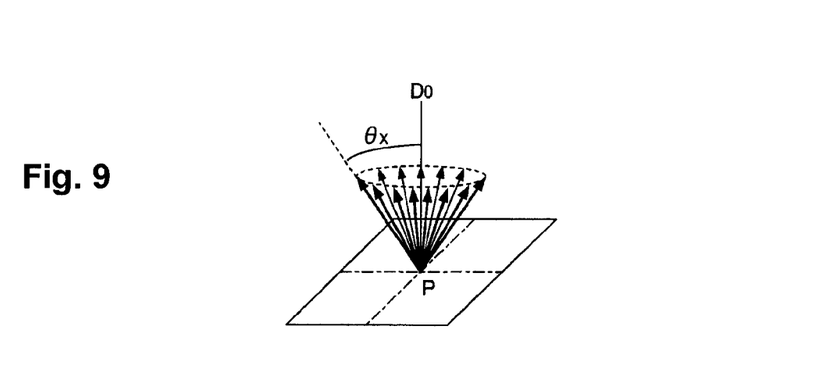
FIG. 9 is a graph showing a relationship between irradiation intensity and a wavelength from the transmissive section in every irradiation angle.
Figure 15:
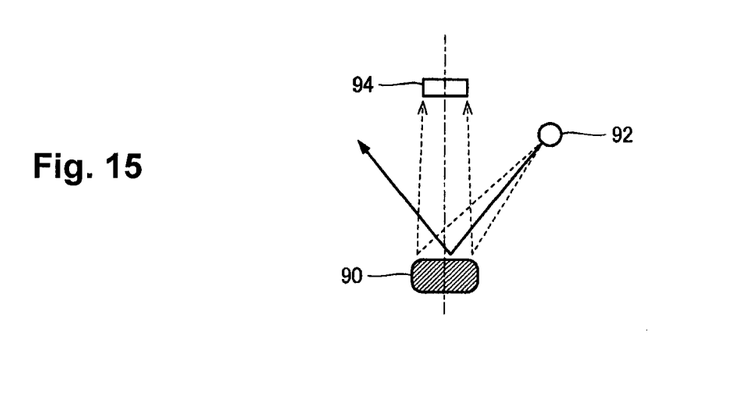
FIG. 15 is an explanatory diagram of a shadow that becomes apparent when a subject is illuminated in a large incident angle.

In a configuration that the resonance length L1 was selected in the above condition, as shown in FIG. 9, the imaging light of the imaging wavelength $\lambda$ (peak wavelength $\lambda 1$) is irradiated in a direction of the target angle $\theta x$ ($\theta x=45°$) with respect to the reference direction D0 in whole periphery of a normal line (line parallel to the reference direction D0) as an axis in any point P of the light emitting section 50. That is, the imaging light of the imaging wavelength $\lambda$, arrives to any point of the surface of the subject 200 from various directions that are inclined in the target angle $\theta x$ with respect to the reference direction D0. Therefore, it is possible to suppress shadows, which reflect the surface structure (texture) of the subject 200, in comparison with the case that the subject 200 is illuminated from one direction that was inclined with respect to the normal line of the surface of the subject 200 as shown in FIG. 15.

Figure 10:
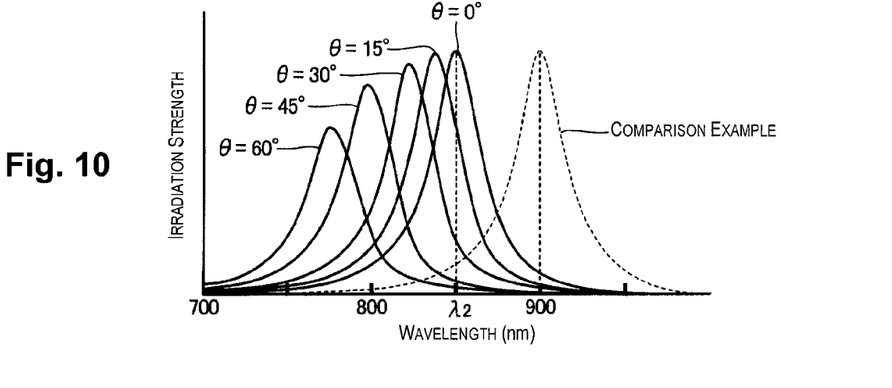
FIG. 10 is a schematic diagram where the imaging light is emitted from the light emitting section.

FIG. 10 is a graph showing a relationship between a wavelength and strength of light emitted from the resonance structure of the transmissive section 60 in the light source section 36 in a plurality of irradiation angles $\theta$ ($\theta=0, 15, 30, 45, 60$ [°]). The vertical axis of FIG. 10 can be seen as same as the transmittance of the transmissive section 60. FIG. 10 shows a characteristic in the case that the resonance length L2 of the resonance structure of the transmissive section 60 is less than the resonance length L1 of the resonance structure of the light emitting section 50 in a solid line. A characteristic for the irradiation angle $\theta$, which is 0°, based on a configuration (hereinafter referred to as "comparison example") presuming that the resonance length L1 and the resonance length L2 are matched each other is shown in a broken line. As is understood from FIG. 10 in the similar manner as FIG. 8, as the irradiation angle $\theta$ of the irradiation light from the resonance structure increases, it tends to reduce the peak wavelength of the irradiation light. Also, as is understood from the comparison example of FIG. 10, as the resonance length L2 of the resonance structure of the transmissive section 60 reduces in comparison to the comparison example (resonance length L1), the peak wavelengths of the light emitted from the resonance structure tend to be shifted to the short wavelength side in comparison to the comparison example as shown in FIG. 10.

From the point of view that the imaging light incident to the transmissive section 60 from the subject 100 side is effectively transmitted to the light receiving section 10 (maintaining the use efficiency of imaging light at high level), it is preferred that the peak wavelength $\lambda 2$ of the irradiation strength (transmittance of the transmissive section 60) from the transmissive section 60 with respect to the reference direction D0 (direction of light axis L0 of lenses 24) matches with the imaging wavelength λ. In consideration of the above tendency, in the present embodiment, as shown in FIG. 10, the resonance length L2 of the resonance structure of the transmissive section 60 is selected so that the peak wavelength λ2 of the irradiation strength from the transmissive section 60 with respect to the reference direction D0 (θ=0°) matches with (come close to) the desired imaging wavelength λ (850 nm). That is, the imaging light of the imaging wavelength λ incident to the transmissive section 60 from the subject 200 side is emitted parallel to the reference direction (θ=0°) from the transmissive section 60.

As shown in FIG. 10 in a broken line, in the comparison example that the resonance length L2 is unified with the resonance length L1, the peak wavelength λ2 of the emitting strength with respect to the reference direction D0 becomes a value approximately 900 nm. As described above, as the resonance length L2 is reduced in comparison with the comparison example (resonance length L1), the peak wavelength λ2 of the light emitted from the resonance structure is shifted to the short wavelength side. Therefore, in the present embodiment, the resonance length L2 is selected to be less than the resonance length L1 (L2<L1). Specifically, the resonance length L1 and the resonance length L2 are selected to be that the resonance length L1 is 10% (preferably 8%) more than the resonance length L2. The resonance length L2 is selected to become approximately one half of the imaging wavelength λ (0.5 wavelength).

In a configuration that the resonance length L2 is less than the resonance length L1 as described above, the peak wavelength λ1 of the irradiation strength from the light emitting section 50 for the target angle θx (θx=45°) inclined with respect to the reference direction D0 and the peak wavelength λ2 of the irradiation strength from the transmissive section 60 with respect to the reference direction D0 (θ=0°) come close to each other in comparison to the comparison example that the resonance length L1 and the resonance length are unified. That is, it is to say that in the present embodiment, it is possible that the resonance length L1 and the resonance length L2 are selected as to approach between the peak wavelength λ1 and the peak wavelength λ2 in comparison with the comparison example (ideally, both the peak wavelength λ1 and the peak wavelength λ2 are matched).

As described above, the imaging light of the desired imaging wavelength λ is emitted from the light emitting section 50 in an illumination direction that inclines the target angle θx with respect to the reference direction D0, and it passes through the transmissive section 60 in the reference direction D0 and progresses to the light receiving section 10 side. Therefore, in the present embodiment, it is possible to take a fine and clear image of the subject 200 while the glares or the shadows of the surface of the subject 200 are suppressed.

<Specific Configurations of Light Emitting Section 50 and Transmissive Section 60>

Figure 11:
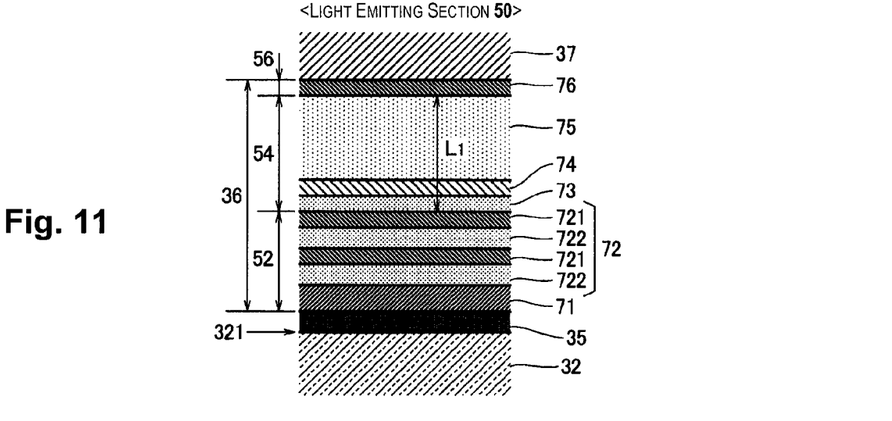
FIG. 11 is a cross-sectional diagram showing a specific configuration of the light emitting section.

The specific configurations of the light emitting section 50 and the transmissive section 60 described above are exemplified below. FIG. 11 is a cross-sectional diagram showing a specific configuration of the light emitting section in the light source section 36.

Figure 12:
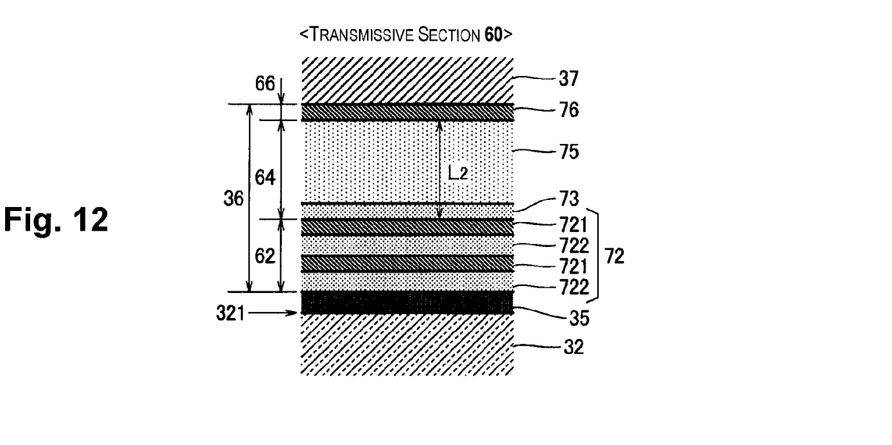
FIG. 12 is a cross-sectional diagram showing a specific configuration of the transmissive section.

FIG. 12 is a cross-sectional diagram showing a specific configuration of the transmissive section 60 in the light source section 36. By the way, in the description below, in a case that a plurality of elements is formed by a common layer (single layer or multiple layers) in the same process, it is written as the phrase "the same layer is formed" or the phrase "the same layers are formed". Each element formed by the same layer is made by a common material, and the respective film thicknesses are roughly corresponded each other.

The reflection layer 52 of the light emitting section 50 is configured to include a basic reflection layer 71 and a dielectric multilayer film 72 as shown in FIG. 11, and the first semi-transmissive reflection layer 62 of the transmissive section 60 is configured to include the dielectric multilayer film 72 as shown in FIG. 12. The dielectric multilayer film 72 of the light emitting section 50 and the dielectric multilayer film 72 of the transmissive section 60 are formed in the same layer, and the first semi-transmissive reflection layer 62 does not include the basic reflection layer 71. That is, the first semi-transmissive reflection layer 62 of the transmissive section 60 has a relationship that the layers from the reflection layer 52 of the light emitting section 50 to the basic reflection layer 71 are omitted.

The basic reflection layer 71 in FIG. 11 is a thin film having light permeability, and is formed on the surface (on the surface 321 of the substrate 32) of the wiring layer 35 by a metal material which is, for example, silver, aluminum, or the like. Specifically, the basic reflection layer 71 is formed by alternatively removing the circular area corresponding to each of the transmissive sections 60 in the thin film having light permeability that was formed in the entire area of the substrate 32.

The dielectric multilayer film 72 in both of the light emitting section 50 and the transmissive section 60 is a dielectric mirror in which a plurality of high refractive index layers 721 and a plurality of low refractive index layers 722 are alternatively laminated. The high refractive index layer 721 and the low refractive index layer 722 are a thin film (dielectric layer) having light permeability, and the refraction index of the high refractive index layer 721 is more than the low refractive index layer 722. Each of the high refractive index layers is formed by, for example, amorphous silicon (a-Si), and each of the low refractive index layers is formed by, for example, silicone nitride (SiNx) or silicon oxide (SiOx). The film thickness of each of the high refractive index layers and each of the low refractive index layers is set to be that the respective optical distances (length of light path) becomes one-quarter of the imaging length λ.

According to the configuration that the reflection layer 52 of the light emitting section 50 was formed by laminating the basic reflection layer 71 and the dielectric multilayer film 72 as exemplified above, it is possible to improve the reflectance (approximately 95%) in comparison with the case that the reflection layer 52 is formed by a single basic reflection layer 71. Also, there is an advantage that the optical loss can be reduced enough by using the dielectric multilayer film 72. By the way, there is a characteristic to absorb visible light in amorphous silicon which is the material of the high refractive index layer 721 so that according to the configuration that the dielectric multilayer film 72 includes the high refractive index layer 721 of amorphous, there is an advantage that it is not necessary to provide an optical filter independently to block the visible light.

The first translucent layer 54 of the light emitting section 50 is configured to include a protection layer 73, a transparent electrode layer 74, and a light emitting layer 75 as shown in FIG. 11, and the second translucent layer 64 of the transmissive section 60 is configured to include the protection layer 73 and the light emitting layer 75 as shown in FIG. 12. The protection layer 73 of the first translucent layer 54 and the protection layer 73 of the second translucent layer 64 are formed in the same layer, and the light emitting layer 75 of the first translucent layer 54 and the light emitting layer 75 of the second translucent layer 64 are formed in the same layer. The second translucent layer 64 does not include the transparent electrode layer 74. That is, the second translucent layer 64 of the transmissive section 60 has a relationship that the layers from the first translucent layer 64 to the transparent electrode layer 74 are omitted.

The protection layer 73 in both of the light emitting section 50 and the transmissive section 60 is a thin film having light permeability, and for example, silicone nitride (SiNx) or silicon oxide (SiOx) are formed on the surface of the dielectric multilayer film 72 in the similar manner as the low refractive layer 722 of the dielectric multilayer film 72. The transparent electrode layer 74 is a conducting layer having light permeability that functions as an electrode (anelectrode) to supply electric current to the light emitting layer 75 in the light emitting section 50. For example, it is made by an electrical conducting material having light permeability such as, for example, Indium Tin Oxide (ITO), or the like, and it is formed to have 20 nm of film thickness, for example, and covers the protection layer 73. Specifically, the transparent electrode layer 74 is formed by alternatively removing the circular area corresponding to each of the transmissive sections 60 in the conducting film having light permeability that was formed in the entire of the surface of the protection layer 73. The transparent electrode layer 74 is electrically connected to the wiring (not shown) of the wiring layer 35 through a conduction hole (not shown) that penetrates through the protection layer 73.

The light emitting layer 75 in both of the light emitting section 50 and the light transmissive section 60 are an electrooptic layer that generates imaging light by supplying the electric current, and is formed by, for example, an Electroluminescence material (organic EL). By the way, the light emitting layer 75 is illustrated as a single layer in FIG. 11 and FIG. 12 for descriptive purposes, but it is possible to form a charge injection layer (hole injection layer, electron injection layer) or a charge transport layer (hole transport layer, electron transport layer) to improve luminance efficiency of the light emitting layer 75.

As shown in FIG. 11 and FIG. 12, the semi-transmissive reflection layer 56 of the light emitting section 50 and the second semi-transmissive reflection layer 66 of the transmissive section 60 are formed in the same layer (reflection conductive layer 76). The reflection conductive layer 76 of the light emitting section 50 functions as electrode (negative electrode) to supply electric current to the light emitting layer 75. That is, in the light emitting section 50, the transparent electrode layer 74 and the reflection conductive layer 76 are opposed each other interposing the light emitting layer 75 so as to form a light emitting element (top mission type organic EL element). The light emitting layer 75 is existed in the transmissive section 60, but the transparent electrode layer 74 is omitted in the transmissive section 60 so that the light emitting element is not formed.

By forming the thin film having the light reflectivity as thin as possible, the semi-transmissive reflectivity of the reflection conductive layer 76 is realized. For example, the reflection conductive layer 76 is formed by an alloy (MgAg) that mixes magnesium (Mg) and silver (Ag). Specifically, from the viewpoint to realize good semi-transmissive reflectivity, the alloy in which the ratio of silver (% by weight) is more than the ratio of magnesium is preferred as a material of the conducting layer. For example, the reflection conductive layer 76 is formed in the film thickness from approximately 20 nm to 30 nm with an alloy in which the ratio of the magnesium is less than 10% and the ratio of silver is more than 90%. By the way, it is possible to realize the semi-transmissive reflectivity by forming numerous fine apertures in the reflection conductive layer 76. The protection layer 37 is formed on the surface of the reflection conductive layer 76 in both of the light emitting section 50 and the transmissive section 60.

In the configuration described above, as is understood from FIG. 11, the resonance length L1 of the resonance structure of the light emitting section 50 corresponds to the distance between the front surface of the dielectric multilayer film 72 (most top layer of the high refractive index layer 721) of the reflection layer 52 and the back surface of the semi-transmissive reflection layer (reflection conductive layer 76). That is, the resonance length L1 of the light emitting section 50 is total value of the film thicknesses of the protection layer 73, the transparent electrode layer 74, and the light emitting layer 75. On the other hand, as is understood from FIG. 12, the resonance length L2 of the resonance structure of the transmissive section 60 corresponds to the distance between the front surface of the dielectric multilayer film 72 of the first semi-transmissive reflection layer 62 and the back surface of the second semi-transmissive reflection layer 66. That is, the resonance length L2 of the transmissive section 60 is a total value of the film thicknesses of the protection layer 73 and the light emitting layer 75. As is understood from the description above, the resonance length L2 is less than the resonance length L1 by the film thickness of the transparent electrode layer 74. By the configuration that the resonance length L1 of the light emitting section 50 and the resonance length L2 of the transmissive section 60 are differentiated in response to existence or non-existence of a part of layers of configuration (transparent electrode layer 74 in the above example) in the respective resonance structures of the light emitting section 50 and the transmissive section 60 as described above, it is possible to differentiate the resonance length L1 and the resonance length L2 with a simple process in comparison with a configuration that the film thickness of the configured layer itself of the resonance structure in the light emitting section 50 and the transmissive section 60 is differentiated.

Modified Example

It is possible for each of the embodiment described above to be changed in various ways. Various aspects are exemplified in detail below. It is possible for two or more of the aspects which are arbitrarily selected from the exemplifications below to be appropriately combined.

(1) In the embodiment described above, the target angle θx that the irradiation strength from the light emitting section 50 becomes a peak in the imaging wavelength λ was 45°, but the target angle θx can be set to any angle that is more than 0°. However, when the target angle θx is extremely large, there is a problem that the components that do not reach to the subject 200 because some of the imaging light emitted from the light emitting section 50 is reflected on the surface 222 of the substrate 22 or the components that do not reach to the light receiving element 14 because it is reflected on the surface 221 of the substrate 22 via the subject 200 increase (that is, the use efficiency of the imaging light is lowered). Therefore, for the target angle θx, an angle that the reflection on the surface 222 of the substrate 22 is appropriately suppressed is selected as an upper limit.

Figure 13:
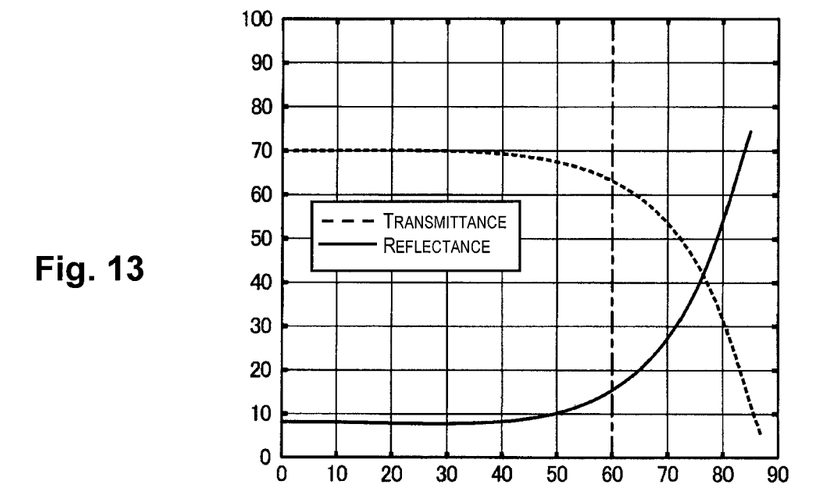
FIG. 13 is a graph showing a relationship between an incident angle with respect to a substrate and transmittance and reflectance.

FIG. 13 is a graph showing a relationship between an incident angle of imaging light (horizontal axis) with respect to a substrate 22 and transmittance and reflectance. The case that AN 100 made by Asahi Glass Co., Ltd. (thickness of 0.5 mm) is provided as the substrate 22 and the imaging light of 830 nm is emitted is simulated. As shown in FIG. 13, when the incident angle is more than 60°, the tendency that the reflectance steeply increases and the transmittance steeply reduces is confirmed. In consideration of the above tendency, it is preferred that an angle as the target angle θx is less than or equal to 60°. Also, in the viewpoint that the glares or the shadows on the surface of the subject 200 are effectively suppressed, it empirically confirms findings that more than or equal to 30° is appropriate as the target angle θx. In consideration of the above tendency, the target angle θx is appropriately selected in the range between more than or equal to 30° and less than or equal to 60°.

(2) Each of the elements that were exemplified in the embodiment described above can be properly omitted. For example, it can be possible to omit the light blocking layer 33 or the plurality of lenses 24. Also, a position relationship of each element that was exemplified in the aspect described above can be properly changed. For example, in the aspect described above, the light emitting section 50 was formed as a top mission type light emitting element, but when the light emitting section 50 is used as a bottom mission type light emitting element, it is possible to form the light source section 36 on the surface 322 of the substrate 32. A configuration that each of the lenses 24 is arranged between the light source section 36 and the light receiving section 10 can be adopted. Also, it is possible that any other element can be intervened between the respective elements that were exemplified in the aspect described above.

(3) In the embodiment described above, the imaging apparatus 100 (a vein sensor) which images an image of veins for biological authorization is exemplified, but the purpose of the invention is arbitrary. For example, it is possible for the invention to be applied to an alcohol detection apparatus which estimates the concentration of alcohol in blood from the images of veins in a living body which is imaged by the imaging apparatus 100 or a medical equipment such as a blood sugar value estimation apparatus, and the like which estimates a blood sugar value from the images of veins in a body which is imaged by the imaging apparatus 100. For the blood alcohol concentration estimation by using an imaging result, or the blood sugar level estimation by using an imaging result, the technologies known to public are arbitrarily adopted. In addition, it is possible to apply the invention to an image reading apparatus which reads an image from a printout. Here, visible light is preferably used as imaging light in a case where the invention is applied to the image reading apparatus.

What is claimed is:

1. An imaging apparatus comprising:
a light receiving section in which a plurality of light receiving elements is arranged; and
a light source section being arranged in a subject side of the light receiving section and including a light emitting section that emits light toward a subject and a plurality of transmissive sections where incident light from the subject side is transmitted to each of the light receiving elements side;
wherein the light emitting section includes a first translucent layer having light permeability that includes a light emitting layer, a semi-transmissive reflection layer that is located in the subject side of the first translucent layer, and a reflection layer that is opposed to the semi-transmissive reflection layer interposing the first translucent layer, so that a resonation structure that the light emitted from the light emitting layer is resonated between the semi-transmissive reflection layer and the reflection layer is formed,
wherein the plurality of the transmissive sections respectively includes a second translucent layer having light permeability, and a first semi-transmissive reflection layer and a second semi-transmissive reflection layer that are opposed each other interposing the second translucent layer, so that a resonation structure that the incident light from the subject side is resonated between the first semi-transmissive reflection layer and the second semi-transmissive reflection layer is formed, and
wherein a first resonance length between the reflection layer and the semi-transmissive reflection layer in the light emitting section is more than a second resonance length between the first semi-transmissive reflection layer and the second semi-transmissive reflection layer in the transmissive section.

2. The imaging apparatus according to claim 1, further comprising: a plurality of lenses being arranged in the subject side of the light source section so that the incident light from the subject side is focused to each of the light receiving elements.

3. The imaging apparatus according to claim 1, wherein the first resonance length and the second resonance length are set as to approach between a peak wavelength of irradiation intensity from the light emitting section in a direction inclined with respect to a reference direction, which is perpendicular to a reflection surface of the resonance structure, and a peak wavelength of irradiation intensity from the transmissive section with respect to the reference direction in comparison to a case that the first resonance length and the second resonance length are matched each other.

4. The imaging apparatus according to claim 3, wherein the first resonance wavelength and the second resonance wavelength are set as to match between the peak wavelength of the irradiation intensity from the light emitting section in the direction inclined with respect to the reference direction and the peak wavelength of the irradiation intensity from the transmissive section with respect to the reference direction.

5. The imaging apparatus according to claim 3, wherein an angle of irradiation direction with respect to the reference direction is more than or equal to 30° and less than or equal to 60°.

6. The imaging apparatus according to claim 1, wherein the reflection layer of the light emitting section includes a basic reflection layer having light permeability and a dielectric multilayer film, and
the first semi-transmissive reflection layer of the transmissive section includes the dielectric multilayer film and does not include the basic reflection layer.

7. The imaging apparatus according to claim 6, wherein the dielectric multilayer film includes a layer formed by amorphous silicon.

8. The imaging apparatus according to claim 1, wherein the semi-transmissive reflection layer of the light emitting section and the second semi-transmissive reflection layer of the transmissive section are formed by a material having light reflectivity and are formed in a same process.

9. The imaging apparatus according to claim 1, wherein the first translucent layer of the light emitting section includes a transparent electrode layer, which has light permeability, and light emitting layer, and the second translucent layer of the transmissive section includes the light emitting layer and does not include the transparent electrode layer.

10. A medical equipment that estimates biometric information from an image taken by an imaging apparatus comprising the imaging apparatus according to claim 1 is included.

* * * * *